(12) United States Patent
De Tommaso

(10) Patent No.: US 6,326,406 B1
(45) Date of Patent: Dec. 4, 2001

(54) CLEAR, INJECTABLE FORMULATION OF AN ANESTHETIC COMPOUND

(75) Inventor: Vincenzo De Tommaso, Basiglio (IT)

(73) Assignee: Westy AG, Vaduz (LI)

( * ) Notice: Subject to any disclaimer, the term of this patent is extended or adjusted under 35 U.S.C. 154(b) by 0 days.

(21) Appl. No.: 09/424,691

(22) PCT Filed: May 14, 1998

(86) PCT No.: PCT/EP98/03004

§ 371 Date: Jul. 18, 2000

§ 102(e) Date: Jul. 18, 2000

(87) PCT Pub. No.: WO98/53805

PCT Pub. Date: Dec. 3, 1998

(30) Foreign Application Priority Data

May 26, 1997 (CH) .................................................. 1224/97

(51) Int. Cl.⁷ ........................... A61K 31/05; A61K 47/32
(52) U.S. Cl. ........................................... 514/731; 424/422
(58) Field of Search ............................. 514/731; 424/422

(56) References Cited

U.S. PATENT DOCUMENTS 5,085,864 * 2/1992 Cannon et al. ...................... 424/450
5,576,012 * 11/1996 Bauer et al. ......................... 424/422

FOREIGN PATENT DOCUMENTS

| 1 089 510 | 3/1959 | (DE) . |
| 3221579 | 12/1983 | (DE) . |
| 0 280 887 | 2/1988 | (EP) . |
| 2 265 357 | 3/1975 | (FR) . |
| 2 298 789 | 9/1996 | (GB) . |
| WO 9632135 | 10/1996 | (WO) . |
| WO 97/10814 | 3/1997 | (WO) . |

* cited by examiner

*Primary Examiner*—Zohrey Fay
*Assistant Examiner*—Brian-Yong Kwon
(74) *Attorney, Agent, or Firm*—Darby & Darby

(57) ABSTRACT

The present invention is directed to a clear, injectable, pharmaceutical composition including propofol, a pharmaceutically acceptable salt of a bile and a lecithin. The present invention is further related to the process for the preparation of the aqueous, injectable pharmaceutical composition including propofol, a pharmaceutically acceptable salt of a bile acid and a lecithin.

22 Claims, No Drawings

CLEAR, INJECTABLE FORMULATION OF AN ANESTHETIC COMPOUND

FIELD OF THE INVENTION

The present invention relates to a clear, injectable, pharmaceutical formulation of propofol.

BACKGROUND OF THE INVENTION

Propofol, whose chemical name is 2,6-bis-(1-methylethyl)phenol, is a known anaesthetic, largely used for general anaesthesia.

The propolol formulation which is presently on the market is a non-transparent, white, oil-in-water emulsion. Similar formulations are described, for example in U.S. Pat. No. 4,799,846 and in GB 2,298,789.

Other injectable propofol preparations have been described. More particularly, WO 96/32135 discloses a pharmaceutical composition in which propofol is used as an inclusion complex with 2-hydroxypropyl-β-cyclodextrine while WO 97/10814 discloses the use of nanodispersions of propofol to be administered by intravenous route.

SUMMARY OF THE INVENTION

The present invention is directed to an aqueous, injectable pharmaceutical composition including propofol, a pharmaceutically acceptable salt of a bile acid and a lecithin.

Another embodiment of the present invention is a process for the preparation of the aqueous, injectable pharmaceutical composition including propofol, a pharmaceutically acceptable salt of a bile acid and a lecithin. The process includes the following steps: (a) adding lecithin to an aqueous solution of the pharmaceutically acceptable salt of the bile acid, the solution having a pH from 4.5 to 6.5; (b) heating the aqueous dispersion at a temperature from 35° to 85° C. for 60 minutes; (c) adding propofol, previously heated at a temperature from 35° to 85° C. to the solution obtained in step (b) heated at a temperature from 35° to 85° C.; and (d) cooling and adding water to the final volume.

DETAILED DESCRIPTION OF THE INVENTION

It has now been found that a transparent injectable formulation of propofol may be obtained by mixing propofol with a bile acid and with a lecithin, More particularly, the formulation presents noteworthy advantages over the presently marketed formulation. Such a formulation is clear, and, hence, the presence of foreign particles, such as glass residues, fibers, undissolved substances and the like, inside the vials or bottles can be easily controlled. This feature is very important for the product safety because, in general, the ready-for-use injectable solutions and, with greater reason, those exclusively used by the intravenous route, as is the case of propofol, must not contain any foreign particles.

Furthermore, the present injectable formulation may be diluted in most of the solutions for infusion, thus allowing the anaesthetist physician to dose the drug with better precision and to administer it with a greater regularity in order to obtain a more precise and safer effect.

Another very important advantage is the fact that the present formulation is stable within a temperature range from +20 to +35° C., which is broader than the stability temperature range (+2° to +25° C.) of the presently marketed formulation. Moreover, the production of the formulation of the present invention does not require any particular or sophisticated apparatus, but it is sufficient to use normal equipment for the production of pharmaceutical formulations for injectable use.

Thus, it is another object of the present invention to provide an aqueous, injectable pharmaceutical composition comprising:
(a) propofol;
(b) a pharmaceutically acceptable salt of a bile salt; and
(c) a lecithin.

The bile salt is advantageously selected from the group consisting of glycocholic acid, cholic acid: chenodesoxycholic acid, taurocholic acid, glycochenodesoxycholic acid, taurochenodesoxycholic acid, litocholic acid, urodesoxycholic acid, dehydrocholic acid, the preferred one being glychocholic acid. The pharmaceutically acceptable salts of the bile acids may be advantageously selected from the group consisting of the sodium, potassium, calcium, magnesium or ammoniun salts. The sodium salt is preferred. Sodium glycocholate is the particularly preferred pharmaceutically acceptable salt of a bile acid.

A lecithin may be soybean lecithin or egg lecithin.

The use of a salt of a cholanic acid in admixture with lecithin for the preparation of mycellar solution of non-steroidal anti-inflammatory compounds, in order to reduce or suppress the local irritation and the hemolytic effects deriving from the parenteral administration of aqueous solutions of the drugs, is described in EP-A-280987.

In the aqueous pharmaceutical formulation of the present invention, propofol is present in an amount from 8 mg to 12 mg per 1 ml of solution, advantageously from 9 mg to 11 mg per ml of solution, preferably in an amount of 10 mg per ml of solution.

The pharmaceutically acceptable salt of the bile acid is present in the aqueous pharmaceutical formulation in an amount, referred to as the free acid, from 25 to 110 mg per 1 ml of solution, preferably from 50 to 60 mg per ml of solution, Lecithin is present in an amount from 40 to 150 mg, preferably from 70 to 80 mg per ml of solution. Soybean lecithin is the preferred lecithin.

According to an advantageous embodiment of the present invention, the aqueous, injectable pharmaceutical composition comprises: from 8 to 12 mg of propofol; from 25 to 110 mg of a bile acid, as a pharmaceutically acceptable salt thereof; and from 40 to 150 mg of a lecithin per ml of solution.

According to a particularly advantageous embodiment of the present invention, in this aqueous, injectable pharmaceutical composition, the bile acid salt is sodium glycocolate and the lecithin is soybean lecithin.

An aqueous, injectable pharmaceutical formulation comprising from 8 to 12 mg, preferable 10 mg of propofol per 1 ml of solution, from 50 to 60 mg of glycocolic acid, as sodium glycocolate per ml of solution and from 70 to 80 mg of soybean lecithin per ml of solution is particularly advantageous.

The water used in the present formulation is water for injectable preparations.

For the manufacture of the present pharmaceutical formulation, the bile acid salt may be straightforwardly used as a starting material or the free acid may be previously salified with a suitable alkalinizing agent which may be, for example, an alkaline metal hydroxide such as sodium, potassium or lithium hydroxide, an alkaline-earth metal hydroxide, such as calcium or magnesium hydroxide, a metal oxide such as magnesium or aluminum oxide, a carbonic acid salt, such as sodium or potassium carbonate, sodium or potassium bicarbonate, a phosphoric acid salt, such as sodium, potassium or calcium phosphate, for example, trisodium phosphate.

It is another object of the present invention to provide a process for the preparation of an aqueous, injectable pharmaceutical composition as mentioned above, which comprises:

(a) adding lecithin to an aqueous solution of the pharmaceutically acceptable salt of the bile acid, the solution having a pH from 4.5 to 6.5;

(b) heating the aqueous dispersion to a temperature from 35° to 85° C. for 60 minutes;

(c) adding propofol, previously heated at a temperature from 35° to 85° C., to the solution obtained in step (b), heated at a temperature from 35° to 85° C.; and (d) cooling and adding water to reach the final volume.

More particularly, the present invention concerns a process for the preparation of an aqueous, injectable pharmaceutical composition containing propofol, a pharmaceutically acceptable salt of a bile acid and a lecithin, as illustrated above, which comprises:

(a) adding lecithin to an aqueous solution of the pharmaceutically acceptable salt of the bile acid, the solution having a pH from 4.5 to 6.5;

(b) heating the aqueous dispersion to a temperature from 35° to 85° C. until a solution is complete;

(c) adding propofol, previously heated at a temperature from 35° to 85° C., to the solution;

(d) cooling to room temperature and adding water to reach the final volume is reached; all the steps being carried out in the substantial absence of oxygen.

The expression "substantial absence of oxygen" means that the solution, during the process, should have a content of oxygen not higher than 1 part per million (p.p.m.), preferable not higher than 0.5 p.p.m.

As set forth above in step (a), the pharmaceutically acceptable salt of the bile acid preferably sodium glycocolate, may be dissolved in water as such or prepared in situ by salification of the bile acid, preferably glycocholic acid, with the selected base, preferably sodium hydroxide. In this latter case, the bile acid, preferably glycocholic acid, is added to an aqueous solution of the base, preferably sodium hydroxide, by adjusting the pH of the solution thus obtained with a pharmaceutically acceptable acid, preferably hydrochloric acid, in order to render the pH compatible with an intravenous administration. The pH is kept at a value from 4.5 to 6.5, advantageously from 5 to 6, preferably about 5.5.

Step (a) is normally carried out at room temperature (20° to 25° C.), but a higher temperature, for example of about 30° C. is also acceptable. The medium is advantageously kept under substantial absence of oxygen by using any technique for removing it, for example by bubbling an inert gas, preferably nitrogen, in the medium and by keeping the medium under inert atmosphere throughout the process. The content of oxygen may be measured according to known methods (for example using an oxygen-sensitive electrode) and kept not higher than 1 p.p.m., preferably lower than 0.5 p.p.m. Lecithin, preferably soybean lecithin, is added under strong stirring, advantageously in an inert atmosphere, preferably under nitrogen stream.

In step (b), the mixture is heated at a temperature from 35° to 85° C. in order to obtain complete dissolution. Usually, a temperature from 35° to 60° C., preferably from 45° to 50° C., is used. Since bile acids and their salts are often surfactants, a foam may be obtained, which dissolves if the mixture is let to stand at rest, advantageously always in substantial absence of oxygen.

In step (c), to the solution thus obtained, heated to 35° to 85° C., preferably at 55° to 60° C., propofol, previously heated at the same temperature, is added under stirring and advantageously in an inert atmosphere, preferably under a nitrogen stream.

In step (d) the clear solution thus obtained, if necessary homogenized, is cooled to room temperature (22° to 25° C.) and diluted with water until the desired volume is reached, preferably by keeping the oxygen concentration of the medium very low, advantageously not higher than 1 p.p.m., preferably lower than 0.5 p.p.m.

The solution thus obtained, when submitted to the conventional operations of pharmaceutical technique for the manufacture of injectable preparations, preferably kept in hermetically closed vessels, is ready for medical use. Preferably, the formulation according to the present invention contains oxygen at a concentration not higher than 0.5 p.p.m. In the vessel containing it (vial or bottle), the head space contains oxygen in an amount preferably not higher than 1%.

EXAMPLE

In a stainless steel reactor equipped with an heating shell, 186 mls of water for injectable preparation were introduced and nitrogen was bubbled thereinto to a concentration of dissolved oxygen lower than 0.5 p.p.m. Keeping the water temperature at about 25° C., 4.8 grams of sodium hydroxide were then added to the water, under gentle stirring and nitrogen stream.

At complete dissolution, a control of the oxygen concentration, to be kept lower than 0.5 p.p.m., was made; then 54.6 grams of glycocholic acid were quickly added in one portion by keeping the mixture at about 30° C. under strong stirring and nitrogen atmosphere. After dissolution, die pH was in the range of 10 to 12. After solubilization of the glycocholic acid, the pH was adjusted to 5.45 to 5.5 with 1N hydrochloric acid, by adding the acid slowly and keeping the solution under strong stirring and nitrogen atmosphere (oxygen concentration lower than 0.5 p.p.m.).

To the solution of sodium glycocholate, 75.6 grams of soybean lecithin were slowly added. Keeping the solution under strong stirring and nitrogen stream, the suspension was then heated at a temperature of 45° to 50° C. under moderate sting and nitrogen atmosphere until the formation of a great amount of foam was observed. The solution was cooled to room temperature and stood for 18 hours under nitrogen pressure, wereafter the complete solubilization of the soybean lecithin was controlled.

The solution was heated at 55° to 60° C. and submitted for 10 minutes to the action of a homogenizer, under a strong nitrogen stream. An amount of 10 grams of propofol, previously heated to 60° C., was slowly poured into the previously obtained solution, keeping it under homogenization and nitrogen stream, at a temperature of 65° to 70° C. The solution was homogenized until a staple of solution diluted 1:1 v/v with water for injectable preparations, showed clear by the naked eye. The solution was cooled to 25° C. by adding 610 mls of water for injectable preparations, very slowly, into the solution at a temperature of 25° C. with a content of dissolved oxygen lower than 0.5 p.p.m. The solution was then kept under gentle stirring and nitrogen stream until the content of dissolved oxygen resulted lower than 0.5 p.p.m.

Then, a vacuum was made in the reactor in order to eliminate the gas dissolved in the solution and water for injectable preparation, with a content of dissolved oxygen lower than 0.5 p.p.m., was added to a volume of 1000 ml. The solution was kept under gentle stirring and nitrogen stream; the value of the pH was controlled in order to keep it at 6.0 to 6.3 (if necessary, the value must be adjusted with 0.2% hydrochoride acid or with 0.2% sodium hydroxide). The amount of dissolved oxygen was controlled and the nitrogen bubbling was continued until an oxygen concentration lower than 0.5 p.p.m. was obtained, The solution was filtered in a sterile unit (class 100) through a 0.22-micron porous membrane, type Durapore® by Millipore, previously controlled and approved for its integrity. Vials or bottles were filled under nitrogen atmosphere, by controlling the amount of residual oxygen in the head space of the vial or bottle in order to keep it lower than 1%

STABILITY ASSAYS

After the initial measurement (time $0=T_0$), controls were made after 30 days ($T_{30}$) and after 60 days ($T_{60}$) from $T_0$.

For the detection of propofol, a method by HPLC, performed with inverse phase column and a UV detector was set up. The specificity and response linearity study in the concentration range of the vials gave satisfactory results to perform the stability suitably.

EXPERIMENTAL MATERIALS AND METHODS

Reagents
  Acetonitrile for HPLC, Merck—Darmstadt
  Deionized water from equipment "Maxima ultra pure water," Elga
  Propofol Standard, Archimica—code 61005, batch no. 95005-0-01 (purity grade:99.8%; Density: 0.955 g/ml).
Standard Solutions
  Standard solution of propofol: in a 100-ml volumetric flask, about 20.0 mg, exactly weighed, of pure product are mixed with water to volume.
  Solutions of propofol samples in vials: tie content of two vials are poured in a perfectly dried flask. 2 ml of the liquid of the vials are pipetted, by a glass pipette, poured in a 100-ml volumetric flask and brought to volume with water.
Equipment
  HPLC CM 4000, Milton Roy, equipped with valve Rheodyne 7125 with a 10-$\mu$l loop;
  detector U.V. Spectromonitor 3100, Milton Roy, with variable wavelength;
  integrator Mega 2, Carlo Erba, witlh paper speed=0.5 cm/min.;
  column: Licbrospher 100 RP-18 (125 cm×4 mm i.d. –5 $\mu$ particle size), Merck-Datrmstadt;
  precolumn: RP 18, Merck-Darmnstadt.
Chromatographic Conditions
  Mobile phase: acetronitrile/water=60:40 v/v
  Flow: 1 ml/min.
  Detector wavelength: 270 nm.
  Average elution time of propofol: 4.30±1.00.
Analytic detection
  For the detection of propofol concentration in the vials, the standard solution of propofol is analyzed by repeating the analysis four times. The solutions of propofol samples in vials are analyzed immediately after the detection of the standard, by repeating the analysis twice. From the comparison of the average areas drawn for peaks of the propofol, the concentration is mg/ml of the active principle in the solution of the vials is calculated.

The results summarized in Tables 1, 2 and 3 show that the solution object of the present patent application remains stable and clear for a period of at least 150 days from the preparation date, within a broad temperature range.

TABLE 1

PROPOFOL 10 mg/ml - Temperature: 5° C.

| DAYS | CONCENTRATION mg/ml | pH | DEGRADATION % |
|---|---|---|---|
| 0 | 8.57 | 6.00 | 0 |
| 30 | 8.58 | 6.17 | +0.12 |
| 60 | 8.62 | 6.12 | +0.58 |
| 120 | 8.48 | n. d.[1] | −1.05 |
| 150 | 8.25 | 6.15 | −3.70 |

[1]n. d. = not determined

TABLE 2

PROPOFOL 10 mg/ml - Temperature: 25° C.

| DAYS | CONCENTRATION mg/ml | pH | DEGRADATION % |
|---|---|---|---|
| 0 | 8.57 | 6.00 | 0 |
| 30 | 8.46 | 6.16 | −1.28 |
| 60 | 8.38 | 6.13 | −2.21 |
| 120 | n. d. | n. d. | n. d. |
| 150 | n. d. | n. d. | n. d. |

TABLE 3

PROPOFOL 10 mg/ml - Temperature: 40° C.

| DAYS | CONCENTRATION mg/ml | pH | DEGRADATION % |
|---|---|---|---|
| 0 | 8.57 | 6.00 | 0 |
| 30 | 8.52 | 6.19 | −0.58 |
| 60 | 8.38 | 6.15 | −2.21 |
| 120 | 8.34 | 6.21 | −2.68 |
| 150 | 8.26 | 6.19 | −3.60 |

What is claimed is:
1. A process for the preparation of a clear, aqueous injectable pharmaceutical formulation of propofol, comprising the following steps:
  (a) adding a lecithin to an aqueous solution of a pharmaceutically acceptable bile acid salt, the aqueous solution having a pH from 4.5 to 6.5;
  (b) heating the aqueous dispersion obtained in step (a) to a temperature from 35° C. to 85° C. to dissolve the lecithin;
  (c) dissolving any foam which is obtained in step (b);
  (d) heating the dispersion obtained in step (c) to a temperature from 35° C. to 85° C.;
  (e) adding propofol to the dispersion obtained in step (d); and
  (f) cooling the dispersion obtained in step (e) and adding water to obtain the clear, aqueous formulation in the desired final volume.
2. The process according to claim 1, carried out in the substantial absence of oxygen.
3. The process according to claims 1, wherein the bile acid salt is sodium glycocholate.
4. The process according to claim 3, wherein the sodium glycocholate is prepared by reacting glycocholic acid with a sodium salt, oxide or hydroxide.

5. The process according to claim 1, wherein the lecithin is soybean lecithin.

6. The process according to claim 1, wherein the bile acid salt and the lecithin are incorporated in the aqueous formulation in amounts of from 25 to 110 mg per ml. and 40 to 150 mg per ml., respectively.

7. The process according to claim 1, wherein the bile acid salt and the lecithin are incorporated in the aqueous formulation in amounts of from 50 to 60 mg per ml. and 70 to 80 mg per ml., respectively.

8. The process according to claim 2, wherein the substantial absence of oxygen is obtained by bubbling an inert gas into the solution in step (a) and maintaining the aqueous media in steps (a)–(d) under the inert atmosphere.

9. The process according to claim 8, wherein the inert gas is nitrogen.

10. The process according to claim 1, wherein the aqueous media in steps (a)–(d) have oxygen contents no higher than 1 p.p.m.

11. The process according to claim 1, wherein:
   (a) the bile acid salt is incorporated in the formulation in an amount, referred to as the free acid, of 25 to 110 mg per 1 ml of the formulation;
   (b) the lecithin is incorporated into the formulation in an amount of 40 to 150 mg per 1 ml of the formulation;
   (c) the propofol is pre-heated prior to addition to the solution obtained in step (d) to a temperature of 35°–85° C.; and
   (d) the process is carried out in an atmosphere having no more than 1 ppm oxygen content, by bubbling nitrogen into the medium during preparation of the formulation.

12. A clear, aqueous injectable pharmaceutical formulation of propofol prepared by the process set forth in claim 1.

13. A clear, aqueous injectable pharmaceutical formulation of propofol prepared by the process set forth in claim 2.

14. A clear, aqueous injectable pharmaceutical formulation of propofol prepared by the process set forth in claim 3.

15. A clear, aqueous injectable pharmaceutical formulation of propofol prepared by the process set forth in claim 4.

16. A clear, aqueous injectable pharmaceutical formulation of propofol prepared by the process set forth in claim 5.

17. A clear, aqueous injectable pharmaceutical formulation of propofol prepared by the process set forth in claim 6.

18. A clear, aqueous injectable pharmaceutical formulation of propofol prepared by the process set forth in claim 7.

19. A clear, aqueous injectable pharmaceutical formulation of propofol prepared by the process set forth in claim 8.

20. A clear, aqueous injectable pharmaceutical formulation of propofol preared by the process set forth in claim 9.

21. A clear, aqueous injectable pharmaceutical formulation of propofol preared by the process set forth in claim 10.

22. A clear, aqueous injectable pharmaceutical formulation of propofol preared by the process set forth in claim 11.

* * * * *